United States Patent [19]

Bihl

[11] Patent Number: 4,526,164
[45] Date of Patent: Jul. 2, 1985

[54] UNIVERSAL SIZE ARM SLING

[75] Inventor: Claudia J. Bihl, Franklin Furnace, Ohio

[73] Assignee: Theodore A. Kirby, Jackson, Ohio

[21] Appl. No.: 512,468

[22] Filed: Jul. 11, 1983

[51] Int. Cl.³ ............................................. A61F 5/40
[52] U.S. Cl. ................................................... 128/94
[58] Field of Search ................... 128/94, 87 R, 82, 83; 224/11, 12, 22

[56] References Cited

U.S. PATENT DOCUMENTS

| | | | |
|---|---|---|---|
| 98,046 | 1/1911 | Wermuth | 128/94 |
| 2,088,927 | 8/1937 | Roy | 128/94 |
| 3,307,538 | 3/1967 | Groll | 128/94 |
| 3,857,388 | 12/1974 | Frankel | 128/87 R |
| 4,198,964 | 4/1980 | Honneffer | 128/94 |

Primary Examiner—Richard J. Apley
Assistant Examiner—Harry Macey
Attorney, Agent, or Firm—Frank H. Foster

[57] ABSTRACT

A universal arm sling suitable for support of either a left arm or a right arm and adjustable to the size of the wearer having an elongated cloth panel with a plurality of tubular passageways at the lower portion. A belt is passed through one tubular passageway selected to yield the appropriate vertical size of the sling and is crossed behind the wearer's back and attached to the upper portion of the elongated cloth.

9 Claims, 5 Drawing Figures

UNIVERSAL SIZE ARM SLING

TECHNICAL FIELD

This invention relates to arm slings and more particularly to arm slings that are adjustable as to size and which may be worn universally by adults or children.

BACKGROUND ART

Numerous arm slings have been devised to provide support for arms. The most recent have attempted to resolve problems of weight distribution of the injured arm on the shoulders in order to provide comfort for the wearer. Other devices have concentrated on means for providing a single sling that can be adjusted to the size of the different individuals who might wear the item. Where some slings have addressed both problems the resultant device is frequently either bulky and cumbersome or not capable of holding the arm snugly near the trunk of the body during wear. Additionally, slings that have addressed these problems are usually rigid and adjustable in only one dimension. For example, they generally do not allow the individual wearing the sling to reposition his arm for comfort while still providing support. The less rigid adjustable slings previously proposed do not prevent the arm from swinging away from the trunk of the body, thus exposing it to further injury.

BRIEF DISCLOSURE OF THE INVENTION

The present invention comprises a sling made of inexpensive materials that may be easily manufactured. The sling consists of an elongated cloth panel having tubular passageways on its lower portion for a strap member to pass through and attachment means on the upper portion for the ends of the strap member to be affixed.

In a preferred embodiment of this invention the elongated cloth panel will be oblong and roughly nexagonal or oval in shape. When in an operable position the lower portion of this cloth panel has fashioned a plurality of tubular passageways. Each passageway is sufficient in width to allow the strap member to pass through. The stitching of the cloth to fashion these tubular passageways must be durable and strong enough to support the weight of the arm being suspended as the strap holds the cloth in place next to the trunk of the wearer's body. The tubular passageways lie transversely and are approximately perpendicular to the longitudinal centerline of the cloth. In this manner, the length of the cloth panel portion of the sling may be adjusted to the size of a wearer by the selection of the appropriate tubular passageway for the strap to pass through.

A primary object of the invention described is to yield a sling with a maximum degree of adjustability to an individual's height or chest size and provides universal wear for support of either arm.

A further object of this invention is to allow the wearer to reposition his supported arm without removing the sling or losing any support in the process. This invention allows the arm to be supported in a position across the person's trunk or at his side. In either position the placement of the strap member through the appropriate tubular passageway causes the arm to be snugly held close to the person's trunk and the arm is not permitted to swing away from the trunk of the body exposing it to further injury.

Another object of this invention is to allow the wearer, once the strap member has been adjusted and passed through the appropriate tubular passageway, to don the sling or remove it unaided and with only the use of the uninjured limb.

A sling constructed as described has only one strap and presents little confusion to one attempting to don the sling.

Figure 1:
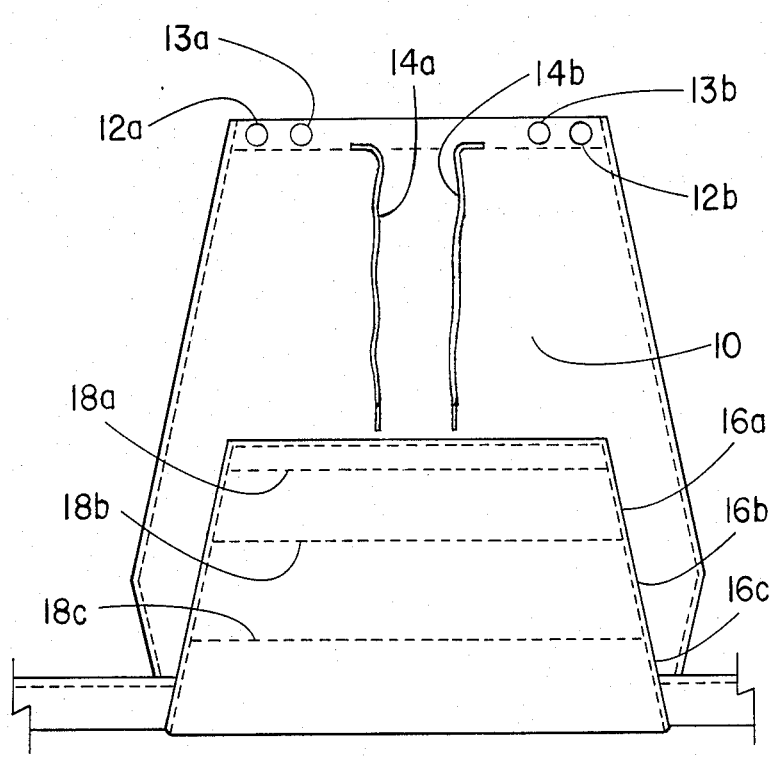
FIG. 1 is a front elevation of the preferred embodiment of the elongated cloth illustrating the placement of its elements.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

Figure 2:
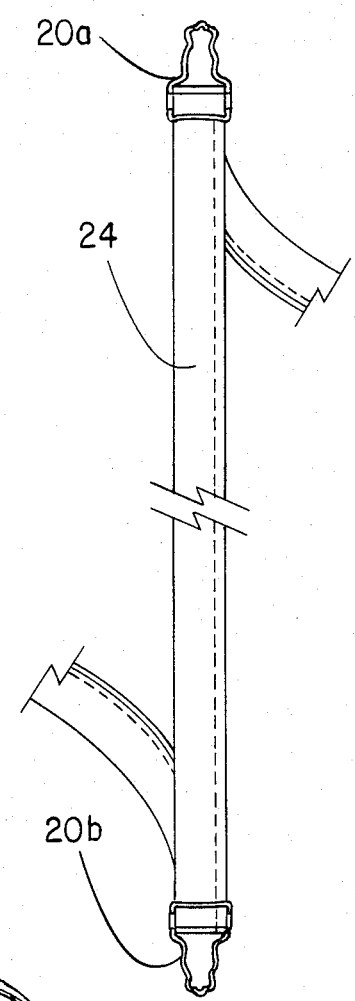
FIG. 2 is a plan view of one embodiment of the strap member illustrating the placement of its elements.
Figure 3:
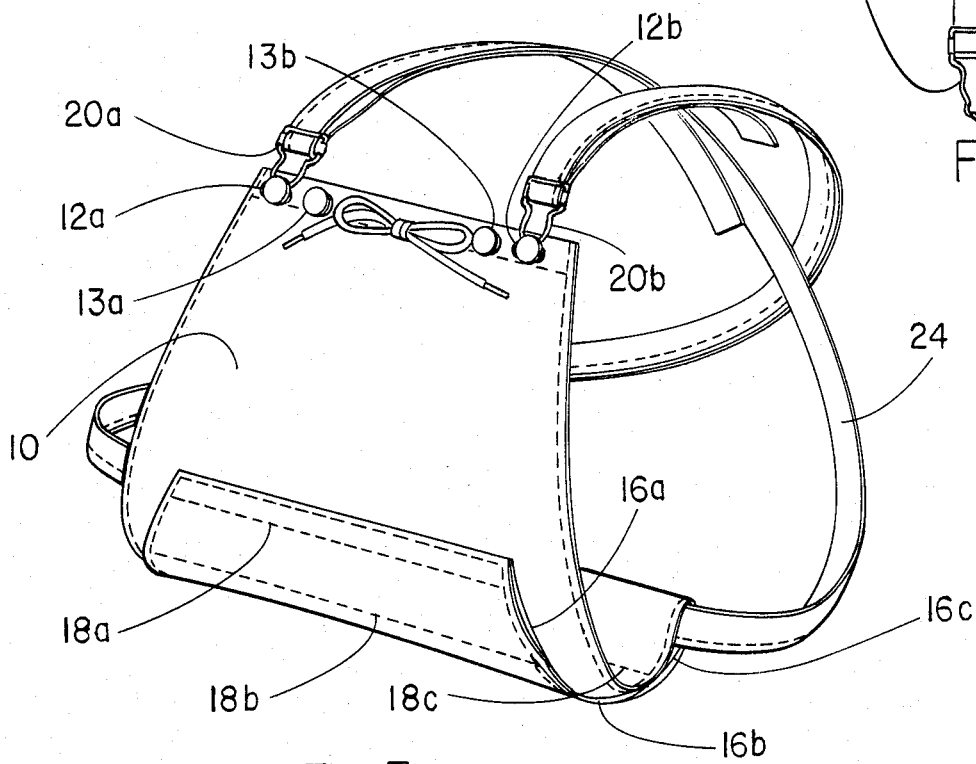
FIG. 3 is a perspective view illustrating the strap passing through a tubular passageway, crossing itself and attaching to the elongated cloth.
Figures 4, 5:
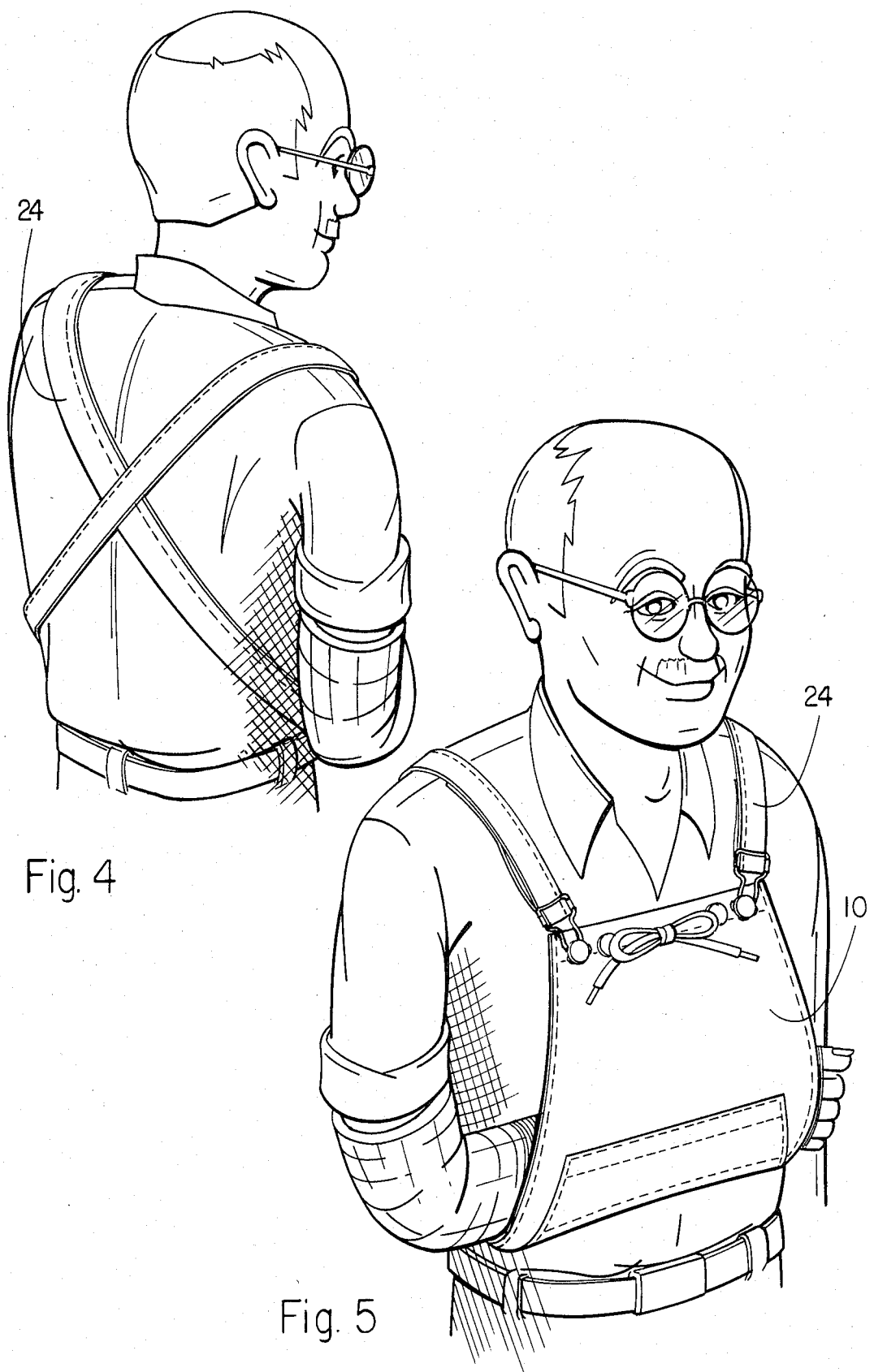
FIG. 4 is a rear elevation demonstrating the position of the strap crossing the wearer's back.
FIG. 5 is a front elevation of the sling in normal wear with the forearm across the trunk of the wearer.

FIGS. 1 and 2 are best utilized for examining the construction of the sling and understanding the relative placement of its elements. FIGS. 3, 4 and 5 illustrate the preferred embodiment of the invention as it would appear while being worn.

FIG. 1 illustrates the body 10 of the sling formed from an elongated flexible panel preferably constructed of cloth. In this embodiment an elongated hexagonal is the shape chosen with a flap folded back over the body 10. The flap is sufficiently long enough to allow stitches 18a, 18b and 18c to be sewn parallel to one another and separated enough to permit a belt 24, described below, to pass through the tubular passageways 16a, 16b and 16c which are formed in the cloth after the stitching is completed. This results in an efficient use of material in the manufacturing of the sling and the necessity to cut a second piece of material to form the tubular passageways is avoided.

Selecting the appropriate tubular passageway 16a, 16b or 16c through which a pass belt 24 adjusts the sling's body 10 for wear by a small, medium or large sized person respectively. The construction of this sling, however, is not limited to an embodiment of only three tubular passageways. Additionally, construction of this invention may be achieved without the use of tubular passageways. Ringlets, belt loops or other appropriate devices may be used in place of the tubular passageways.

In each corner opposite the tubular passageways 16a, 16b and 16c are a plurality of attachment devices 12a, 12b, 13a and 13b. Placement of these devices are such that the wearer may adjust the width of the body 10 of the cloth panel to his chest. In the preferred embodiment the attachment devices are metal buttons, however, other suitable devices such as Velcro pads, ties, buckles or snaps may be used. In addition to a plurality of attachment devices 12a, 12b, 13a and 13b or in an alternative embodiment using only two attachment devices 12a and 12b are two strings 14a and 14b which may be tied to make further horizontal adjustment in the distance between the attachment devices 12a, 12b, 13a and 13b to give a better fit across the wearer's chest.

FIG. 2 illustrates a belt 24 made of cloth or other suitable material. At either end of the belt 24 is an attachment device 20a or 20b for appropriate use with the attachment devices 12a and 12b used on the body 10 of the sling. In the preferred embodiment attachment devices 20a and 20b are metal clips capable of being fastened to or released from the two metal buttons with the use of only one hand. Additionally, the clips may be used to adjust the length of the belt 24 by pulling or loosening either end of belt 24 through the clips. The length of belt 24 must be sufficiently long enough to fit any wearer. In the preferred embodiment excess material of belt 24 not utilized by a smaller wearer is to be severed and discarded.

FIG. 3 illustrates the positioning of the elements of the sling as they would appear through tubular passageway 16c to give the body 10 of the sling its maximum elongated size. Belt 24 is crossed behind the wearer's back and affixed to the sling's body 10 by attachment of devices 20a and 20b to attachment devices 12a and 12b respectively.

An alternative embodiment is a sling as described that has one terminal point of the strap permanently affixed to the elongated cloth. This version removes the added expense of attachment devices, but gives the wearer less flexibility in fitting the sling. Where neither attachment is permanently affixed the sling retains the greatest degree of universal wear. With two removable attachments the sling may be easily put on or removed regardless of which limb the wearer has incapacitated. Also, this combination provides additional flexibility for the wearer to adjust the sling to a comfortable fit.

FIG. 4 illustrates the belt 24 crossed on the back of the wearer. The ends of belt 24 are not affixed at the cross point so as to give the wearer complete freedom to shift his arm about in the sling or to adjust the belt 24 through either attachment device 20a or 20b.

Referring to FIG. 5, the elements of the sling are illustrated in use. To don the sling the belt 24 is passed through the appropriate tubular passageway 16a, 16b or 16c to allow for the vertical size of the wearer. The attachment device 12a or 12b on the same side as the injured limb is affixed to the attachment device on the end of belt 24 protruding out of the opening of the tubular passageway 16a, 16b or 16c on the side of the sling's body 10 opposite the injured limb. The sling is then put on over the wearer's head and positioned over his anterior trunk. The injured arm is placed into the lower portion of the sling by wrapping the body 10 of the sling over and up under the injured arm. The lower portion of the body 10 of the sling through which belt 24 passes is between the injured arm and the anterior trunk of the wearer. The wearer then uses his uninjured arm to flip the end of belt 24, remaining unattached across his back and over the shoulder of his uninjured arm. Final attachment of this end is made to the body 10 of the sling.

FIG. 5 also illustrates strings 14a and 14b tied to adjust the width of the body 10 of the sling across the wearer's chest.

The sling as described supports the wearer's injured arm whether it be his left or right arm. The support is provided by the lower portion of the body 10 of the sling which partially wraps the forearm of the injured limb. The amount of cloth supporting the forearm is determined by selection of the width of the body 10 of the sling and also adjustable by the appropriate tubular passageway 16a, 16b or 16c. In the preferred embodiment illustrated in FIGS. 1 and 5 the amount of forearm support provided by tubular passageway 16a is less than that provided by tubular passageway 16c because the folded flap portion of the body 10 of the sling tapers inwardly on both sides. The weight of the arm supported by this sling is distributed by belt 24 to each shoulder and not the neck of the wearer.

While certain preferred embodiments of the present invention have been disclosed in detail, it is to be understood that various modifications in its structure may be adopted without departing from the spirit of the invention or the scope of the following claims.

I claim:

1. A universal arm sling for support of either a left arm or a right arm comprising:
    (a) an elongated flexible panel having an upper portion and a lower portion;
    (b) a plurality of substantially parallel passageways formed laterally across said lower portion of said elongated flexible panel the passageways being formed one above the other;
    (c) a flexible belt with two opposite ends and extending through one of said passageways thereby permitting selectable adjustability in the vertical length of said elongated flexible panel; and
    (d) fastener means affixed to the ends of said flexible belt and to the upper portion of said elongated flexible panel for releasably attaching the ends of said belt to the top of said panel.

2. A universal arm sling for support of either a left arm or a right arm as recited in claim 1 further comprising
    means associated with said upper portion for adjusting the width thereof.

3. A universal arm sling for support of either a left arm or a right arm as recited in claim 2 wherein said adjusting means comprises two strings affixed at laterally spaced points for being drawn and tied together for adjustment of said upper portion of said elongated flexible panel in width.

4. A universal arm sling for support of either a left arm or a right arm as recited in claim 2 wherein said fastener means to affix said ends of said flexible belt to said elongated flexible panel comprises clip and button fasteners.

5. A universal arm sling for support of either a left arm or a right arm as recited in claim 4 wherein a plurality of said buttons are located approximately horizontally across said upper portion of said elongated flexible panel.

6. A universal arm sling for support of either a left arm or a right arm as recited in claim 2 wherein said plurality of passageways are formed by a double layer having a plurality of lateral, parallel stitches across said lower portion of said elongated panel and through the double layer.

7. A universal arm sling for support of either a left arm or a right arm as recited in claim 6 wherein said plurality of parallel stitches are perpendicular to a centerline extended along said elongated flexible panel.

8. A universal arm sling for support of either a left arm or a right arm as recited in claim 2 wherein the width of said lower portion of said elongated panel tapers downwardly and inwardly.

9. A universal arm sling for support of either a left arm or a right arm as recited in claim 1 wherein said flexible belt further comprises adjustment means for adjusting the length thereof.

* * * * *